United States Patent
McMahon et al.

(10) Patent No.: US 7,247,742 B2
(45) Date of Patent: Jul. 24, 2007

(54) RECYCLING POLYETHYLENE NAPHTHALATE CONTAINING MATERIALS IN A PROCESS TO PRODUCE DIESTERS

(75) Inventors: Rosemary F. McMahon, Wheaton, IL (US); John A. Macek, Aurora, IL (US); Gregory P. Hussmann, Batavia, IL (US); Michael J. Panzer, Lockport, IL (US); Raymond J. Eifert, Warrenville, IL (US); David A. Young, Hartselle, AL (US); Allen B. Mossman, Wheaton, IL (US); J. Deven Cleckler, Decatur, AL (US)

(73) Assignee: BP Corporation North America Inc., Warrenville, IL (US)

( * ) Notice: Subject to any disclaimer, the term of this patent is extended or adjusted under 35 U.S.C. 154(b) by 435 days.

(21) Appl. No.: 10/849,750

(22) Filed: May 20, 2004

(65) Prior Publication Data

US 2005/0261512 A1    Nov. 24, 2005

(51) Int. Cl.
*C07C 67/08* (2006.01)
*C07C 69/76* (2006.01)

(52) U.S. Cl. .......................... 560/100; 560/96; 560/98
(58) Field of Classification Search ................ 560/80, 560/77, 98, 96, 100
See application file for complete search history.

(56) References Cited

U.S. PATENT DOCUMENTS

| | | | |
|---|---|---|---|
| 2,833,816 A | 5/1958 | Saffer et al. | 260/524 |
| 3,042,709 A | 7/1962 | Convery | 260/475 |
| 3,870,754 A | 3/1975 | Yamashita et al. | 260/524 |
| 4,873,386 A | 10/1989 | Hagen et al. | 585/471 |
| 4,933,491 A | 6/1990 | Albertins et al. | 562/416 |
| 4,950,786 A | 8/1990 | Sanchez et al. | 562/416 |
| 4,950,825 A | 8/1990 | Sikkenga et al. | 585/320 |
| 5,026,917 A | 6/1991 | Hagen et al. | 568/323 |
| 5,030,781 A | 7/1991 | Sikkenga et al. | 585/320 |
| 5,034,561 A | 7/1991 | Sikkenga et al. | 585/411 |
| 5,262,560 A | 11/1993 | Holzhauer et al. | 560/78 |
| 5,350,874 A | 9/1994 | Behrens et al. | 560/80 |
| 5,554,657 A | 9/1996 | Brownscombe et al. | 521/48 |
| 5,635,584 A | 6/1997 | Ekart et al. | 528/271 |
| 6,136,869 A | 10/2000 | Ekart et al. | 521/48.5 |
| 6,211,398 B1 | 4/2001 | Pell, Jr. | 560/78 |

*Primary Examiner*—Taylor Victor Oh
(74) *Attorney, Agent, or Firm*—Kelly L. Cummings; Nirav Patel

(57) ABSTRACT

A process for preparing a dialkylester of a naphthalenedicarboxylic acid comprising directing a liquid phase reaction mixture comprising a low molecular weight alcohol, a naphthalenedicarboxylic acid, a dialkylester of a naphthalenedicarboxylic acid, and a polyethylene naphthalate containing material, at a given temperature and pressure through series arranged reaction zones and subsequently removing a product comprising a dialkylester formed by the reaction of the naphthalenedicarboxylic acid and the polyethylene naphthalate containing material with the low molecular weight alcohol from a reaction zone. This invention is also directed to a process for preparing a purified dialkylester of a naphthalenedicarboxylic acid comprising a series of crystallization and distillation steps, and combinations thereof.

35 Claims, No Drawings

RECYCLING POLYETHYLENE NAPHTHALATE CONTAINING MATERIALS IN A PROCESS TO PRODUCE DIESTERS

BACKGROUND OF THE INVENTION

The diesters of naphthalenedicarboxylic acids are useful for preparing a variety of polymeric materials such as polyesters or polyamides. One particularly useful diester is dimethyl-2,6-naphthalenedicarboxylate (DM-2,6-NDC). DM-2,6-NDC, for example, can be condensed with ethylene glycol to form polyethylene naphthalate (PEN), a high performance polyester material. Fibers and films made from PEN have considerably improved strength and superior thermal properties relative to, for example, polyethylene terephthalate. For this reason, PEN is an exceptional material for preparing commercial articles such as thin films which can be used, for example, for the manufacture of magnetic recording tape and electronic components. Additionally, because of its superior resistance to gas diffusion, and particularly to the diffusion of carbon dioxide, oxygen and water vapor, films made from PEN are useful for manufacturing food containers, especially the so-called "hot fill" food containers. PEN is also useful for preparing high strength fibers which can be used to manufacture tire cord, for example.

In order to prepare high quality PEN suitable for commercial use, it is necessary to start with purified DM-2,6-NDC. The purified DM-2,6-NDC must be low in color, substantially free of organic and inorganic impurities, and low in particulate matter.

DM-2,6-NDC is most readily prepared by the esterification of 2,6-naphthalenedicarboxylic acid (2,6-NDA) with methanol. The 2,6-NDA is conveniently prepared by the oxidation of a 2,6-dialkyl- or 2-alkyl-6-acyl naphthalene compound using molecular oxygen and catalyzed by a catalyst comprising cobalt, manganese and bromine components. During this oxidation reaction, impurities such as 6-formyl-2-naphthoic acid (FNA), trimellitic acid (TMLA) and various brominated compounds are produced. Although in some instances it would be desirable to use 2,6-NDA directly for the preparation of PEN because of its high melting point (>300° C. with decomposition) and extremely low solubility in ordinary solvents, 2,6-NDA is extremely difficult to purify to acceptable levels by standard purification techniques such as distillation and recrystallization. These difficulties in purifying 2,6-NDA are partially overcome by converting 2,6-NDA to its dimethyl ester, DM-2,6-NDC. DM-2,6-NDC can be distilled and it can be recrystallized from solvents such as methanol or from one or more aromatic solvents. However, even though DM-2,6-NDC can be purified by treatments such as distillation or recrystallization, purifying DM-2,6-NDC to a purity acceptable for use in the aforementioned manufactured articles remains a problem in the art. For example, the FNA produced during the oxidation of dialkylnaphthalene is incorporated (as a methyl ester) into DM-2,6-NDC during the esterification of 2,6-NDA and is very difficult to remove or reduce to acceptable low levels. In particular, cobalt and manganese oxidation catalyst metals used for the preparation of 2,6-NDA are also typically carried over into the esterification reaction as impurities. This is because a certain amount of the oxidation catalyst metal is complexed tightly to TMLA and other oxidation by-products and is not removed in the oxidation mother liquor when the oxidation mother liquor is separated from the solid 2,6-NDA. Catalyst metals cause problems in the downstream operations used for purifying the DM-2,6-NDC by, for example, causing a thickening of the distillation bottoms and plugging of the distillation column. These catalyst metals must be removed prior to the distillation of DM-2,6-NDC.

Finally, particulate contamination in the DM-2,6-NDC must be eliminated or reduced to very low levels. Particulate contamination in the DM-2,6-NDC causes particulate contamination in PEN made from the DM-2,6-NDC. These particulate contaminants render the PEN unsuitable for manufacturing the thin, high-strength film used to prepare, for example, recording tape. These particulate impurities, which range in size down to below 1.5 microns, can arise from a variety of sources. For example, they may be oxidation catalyst particles. They may also be derived from filtering and drying operations where DM-2,6-NDC is dissolved in a solvent, recrystallized, separated from the recrystallization mother liquor by filtration and dried to remove excess solvent. Inevitably, a considerable amount of particulates contaminate the DM-2,6-NDC product in these processes. Regardless of the source, particulate contamination in the DM-2,6-NDC product is undesirable.

PEN or certain materials made from PEN can generate a relatively high rate of "scrap" or off-specification material. This material can be judged to be scrap for various reasons, including failure to meet color specifications, failure to meet molecular weight or intrinsic viscosity specifications, improper crystallinity, high diethylene glycol content, contamination by extraneous materials, heels from equipment drainage, and/or any other defect which would prohibit using the affected PEN in finished goods. Due to the high value of the contained naphthalate fraction in PEN, however, it is uneconomical to simply discard off-specification PEN. Thus, there is a need in the art to economically and conveniently reclaim the naphthalate value of PEN while simultaneously satisfying the stringent purity requirements of the final DM-2,6-NDC product.

SUMMARY OF THE INVENTION

One aspect of this invention is a process for preparing a dialkylester of a naphthalenedicarboxylic acid. The process comprises directing a liquid phase reaction mixture comprising a low molecular weight alcohol, a naphthalenedicarboxylic acid, a dialkylester of a naphthalenedicarboxylic acid, and a polyethylene naphthalate containing material, at a temperature range of about 500° F. to about 700° F. and at a pressure in the range of about 5 to about 250 atmospheres absolute through series arranged reaction zones. During this process, a naphthalenedicarboxylic acid, a polyethylene naphthalate containing material, and a low molecular weight alcohol are introduced to an upstream reaction zone. A dialkylester product formed by the reaction of the naphthalenedicarboxylic acid and polyethylene naphthalate containing material with the low molecular weight alcohol from a downstream reaction zone is removed.

In addition, the process can occur in a vertically arranged, compartmented reactor. The compartmented reactor has at least an upper and lower compartment with the compartments being separated by a dividing means having an opening to permit the upward flow of the esterification reaction mixture between reactor compartments. The low molecular weight alcohol and the naphthalenedicarboxylic acid and the polyethylenenaphthalate containing material are added to the lower compartment or compartments, and a reaction product mixture comprising a diester of naphthalenedicarboxylic acid is removed from the upper reactor compartment.

Another aspect of this invention is a process for preparing a dialkylester of a naphthalenedicarboxylic acid where low molecular weight alcohol is added to the reaction zone and simultaneously removed from the reaction zone such that the ratio of the rate of removal of the alcohol in pounds per hour from the reaction zone in the gas phase to the rate of addition of the alcohol to the reaction zone in pounds per hour is about 0.5:1 to about 0.99:1.

Yet another aspect of this invention is a process for preparing a purified dialkylester of a naphthalenedicarboxylic acid comprising a series of crystallization and distillation steps, and combinations thereof.

Surprisingly, we have found that the PEN containing materials react with the low molecular weight alcohol which is present in excess to form crude DM-2,6-NDC, which can be recovered and purified. The crude DM-2,6-NDC derived from the PEN containing materials may be processed along with the main flow of crude DM-2,6-NDC that was made from reaction of the low molecular weight alcohol with 2,6-NDA. The ethylene glycol byproduct and products derived from the reaction of ethylene glycol with itself or with the low molecular weight alcohol may be processed out of the unit as a consequence of normal solvent processing and purging of impurities using any suitable techniques. Other impurities which are present in the PEN are economically removed by the same unit operations which purify the DM-2,6-NDC produced by the main normal process flow to its final form. Due to the conditions in and design of the esterification reactor, no new catalyst or other components are needed to accomplish the cleavage and transesterification reactions. This is a benefit because if no new ingredients are added for reaction, they need not be subsequently removed.

DESCRIPTION OF THE INVENTION

The naphthalenedicarboxylic acids useful in the method of this invention are selected from: 1,2-, 1,3-, 1,4-, 1,5-, 1,6-, 1,7-, 1,8-, 2,3-, 2,6-, or 2,7-naphthalenedicarboxylic acid, however, 2,6- and 2,7-naphthalenedicarboxylic acid are preferred. Most preferred is 2,6-naphthalenedicarboxylic acid. Any known method for preparing these naphthalenedicarboxylic acids can be used. The process of this invention is particularly suitable for esterifying a naphthalenedicarboxylic acid prepared by the liquid phase, heavy metal catalyzed oxidation of a dialkyl- or alkyl-acylnaphthalene compound. Such dialkyl or alkylacylnaphthalene compounds that can be oxidized by a liquid phase, heavy metal catalyzed oxidation reaction include components having the following structure

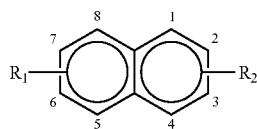

and are independently selected from a hydrocarbonyl group having 1 to about 6 carbon atoms, an acyl group having 2 to about 6 carbon atoms or a formyl group. Specific examples of such naphthalene compounds include 2,6-dimethylnaphthalene, 2-methyl-6-acetyinaphthalene, 2-methyl-6-butrylnaphthalene, 1,4-dimethylnaphthalene, 2,3-dimethylnaphthalene, 2,6-dimethylnaphthalene, 2,6-diisopropylnaphthalene. U.S. Pat. Nos. 5,034,561; 5,030,781 and 4,950,825, issued to Sikkenga, et al disclose methods for preparing dimethylnaphthalene. U.S. Pat. No. 5,026,917 issued to Hagen et al discloses a process for preparing 2-methyl-6-acetylnaphthalene is disclosed. U.S. Pat. No. 4,873,386 issued to Hagen et al discloses a process for preparing 2,6-diethyinaphthalene.

The most preferred aromatic feed compound for preparing the naphthalenedicarboxylic acid is 2,6-dimethylnaphthalene. Oxidation of 2,6-dimethylnaphthalene produces 2,6-naphthalenedicarboxylic acid which, as described hereinabove, is a suitable monomer for preparing PEN. Furthermore, 2,6-dimethylnaphthalene is superior to, for example, 2,6-diethyl- or 2,6-diisopropylnaphthalene because it is lower in molecular weight and the yield of 2,6-naphthalenedicarboxylic acid per given weight of 2,6-dialkylnaphthalene compound is greater for 2,6-dimethylnaphthalene than for 2,6-diethyl- or 2,6-diisopropylnaphthalene.

Methods for conducting the liquid phase, heavy metal catalyzed oxidation of an alkyl- or acyl-substituted aromatic compounds—such as the naphthalene compounds described hereinabove—to the corresponding aromatic carboxylic acid are well known in the art. For example, U.S. Pat. Nos. 4,950,786; 4,933,491; 3,870,754 and 2,833,816 disclose such oxidation methods. In general, suitable heavy metal oxidation catalysts include those metals having an atomic number of about 21 to about 82, inclusive. The preferred oxidation solvent is a low molecular weight monocarboxylic acid having 2 to about 8 carbon atoms, inclusive, preferably it is acetic acid or mixtures of acetic acid and water. A promoter such as a low molecular weight ketone having 2 to about 6 carbon atoms or a low molecular weight aldehyde having 1 to about 6 carbon atoms can also be used. Bromine promoter compounds known in the art such as hydrogen bromide, molecular bromine, sodium bromide and the like can also be used. A source of molecular oxygen is also required; typically air is used.

A particularly suitable method for oxidizing dialkyl or alkylacylnaphthalene compounds, and particularly 2,6-dimethylnaphthalene, to naphthalenedicarboxylic acids is disclosed in U.S. Pat. No. 4,933,491 to Albertins et al. Suitable solvents for such liquid phase oxidation reaction of dialkyl or alkylacylnaphthalene compounds include low molecular weight carboxylic acids such as benzoic acid, any aliphatic $C_2$-$C_6$ monocarboxylic acid such as acetic acid, propionic acid, n-butyric acid, isobutyric acid, n-valeric acid, trimethylacetic acid, caproic acid, and water. Preferably the solvent is a mixture of water and acetic acid, which mixture is preferably 1 to 20 weight percent water. The source of molecular oxygen employed in such liquid phase oxidation of the dialkyl or alkylacylnaphthalene compounds can vary in molecular oxygen content from that of air to oxygen gas. Because of economy, air is the preferred source of molecular oxygen.

The catalyst employed in such oxidation of the dialkyl or alkylacyinaphthalene compounds comprises a bromine containing compound and at least one of a cobalt and manganese containing compound. Preferably, the catalyst comprises cobalt, manganese, and bromine containing components. The ratio of cobalt (calculated as elemental cobalt) in the cobalt component of the catalyst to dialkyl or alkylacylnaphthalene compound in the liquid phase oxidation is in the range of about 0.1 to about 100 milligram atoms (mga) per gram mole of dialkyl or alkylacylnaphthalene compound. The ratio of manganese (calculated as elemental manganese) in the manganese component of the catalyst to cobalt (calculated as elemental cobalt) in the cobalt component of the catalyst in the liquid phase oxidation is in the range of from about 0.1 to about 10 mga per mga of cobalt. The ratio of bromine (calculated as elemental bromine) in the bromine component of the catalyst to total cobalt and manganese (calculated as elemental cobalt and elemental manganese) in the cobalt and manganese components of the catalyst in the liquid phase oxidation is in the range of from about 0.1 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1.0 to 1.5:1.0 bromine to total cobalt and manganese milligram atom ratio is provided by a suitable bromine source such as elemental bromine ($Br_2$), or ionic bromide (e.g., HBr, NaBr, KBr, $NH_4$ Br, etc.), or organic bromides which are known to provide bromide ions at the operating temperature of the oxidation (e.g., bromobenzenes, benzylbromide, tetrabromoethane, ethylenedibromide, etc.). The total bromine in molecular bromine and ionic bromide is used to determine satisfaction of the elemental bromine to total cobalt and manganese milligram atom ratio of 0.1:1.0 to 1.5:1.0. The bromine ion released from the organic bromides at the oxidation operating conditions can be readily determined by known analytical means. Tetrabromoethane, for example, at operating temperatures of 335° F. to 440° F., has been found to yield about 3 effective gram atoms of bromine per gram mole.

In operation, the minimum pressure at which the oxidation reactor is maintained is that pressure which will maintain a substantial liquid phase of the dialkyl or alkylacylnaphthalene compound and at least 70 weight percent of the solvent. The dialkyl or alkylacylnaphthalene compound and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 atmospheres to about 35 atmospheres, and typically are in the range of from about 10 atmospheres to about 30 atmospheres. The temperature range within the oxidation reactor is generally from about 250° F., preferably from about 350° F. to about 450° F., more preferably to about 420° F. The solvent residence time in the oxidation reactor is generally from about 20 to about 150 minutes and preferably from about 30 to about 120 minutes.

The oxidation can be performed either in a batch, continuous, or semicontinuous mode. In the batch mode, the dialkyl or alkylacyinapthalene compound, solvent and the catalyst components are initially introduced batchwise into the reactor, and the temperature and pressure of the reactor contents are then raised to the desired levels for the commencement of the oxidation reaction. Air is introduced continuously into the reactor. After commencement of the oxidation reaction, for example, after all of the dialkyl or alkylacylnaphthalene compound has been completely introduced into the reactor, the temperature of the reactor contents is raised. In the continuous mode, each of the dialkyl or alkylacylnaphthalene compound, air, solvent, and catalyst are continuously introduced into the reactor, and a product stream comprising naphthalenedicarboxylic acid and catalyst components dissolved in the solvent is withdrawn from the reactor. In the semicontinuous mode, the solvent and catalyst are initially introduced into the reactor and then the dialkyl or alkylacylnaphthalene compound and air are continuously introduced into the reactor. For large-scale commercial operation it is preferable to use a continuous oxidation process. In such a process using 2,6-dimethylnaphthalene as the feed, the weight ratio of monocarboxylic acid solvent to 2,6-dimethylnaphthalene is preferably about 2:1 to about 12:1, the mga ratio of manganese to cobalt is about 5:1 to about 0.3:1, the mga ratio of bromine to the total of cobalt and manganese is about 0.3:1 to about 0.8:1, and the total of cobalt and manganese, calculated as elemental cobalt and elemental manganese is at least about 0.40 weight percent based on the weight of the solvent, and the oxidation reaction temperature is about 370° F. to about 420° F. Acetic acid is the most suitable solvent for such preferred continuous oxidation of 2,6-dimethylnaphthalene.

Subsequent to the oxidation reaction, the oxidation reaction mixture is typically cooled to promote the crystallization of the naphthalenedicarboxylic acid from the reaction mixture; and the naphthalenedicarboxylic acid is partitioned (i.e. separated) from the oxidation reaction mixture by any suitable means for separating a solid from a liquid phase, for example, by centrifugation, filtration and the like. The separated naphthalenedicarboxylic acid can be washed with one or more solvents either at ambient or, preferably, an elevated temperature. Most suitably the wash solvent is water, acetic acid or other low molecular weight aliphatic carboxylic acid or mixtures of water and a low molecular weight carboxylic acid. The crude naphthalenedicarboxylic acid can be dried before esterification.

After the 2,6-naphthalenedicarboxylic acid is prepared, the next step comprises esterifying it with a low molecular weight alcohol to produce esterified 2,6-naphthalenedicarboxylate. In addition, PEN containing materials are added to the feed to the esterification reactor. As used herein, "PEN containing material" describes PEN homopolymer or PEN film materials or other PEN-containing substances that are added to the feed to the esterification reactor. The PEN containing material comprises up to about 20 weight percent of the 2,6-NDA in the feed. Although some impurities such as brominated 2,6- naphthalenedicarboxylic acid and other brominated compounds, 6-formyl-2-naphthoic acid (FNA), 6-methyl-2-naphthoic acid, trimellitic acid (TMLA), and cobalt and manganese catalysts are partly removed during the process of isolating 2,6 NDA from the oxidation reaction mixture, unacceptable levels of impurities remain with the 2,6-NDA, are consequently carried over to the esterification reaction, and must be removed during purification of DM-2, 6-naphthalenedicarboxylate.

The alcohols that are useful in the esterification process of this invention are low-molecular weight alcohols having 1 to about 6 carbon atoms, for example: methanol, ethanol, n-propanol, isopropanol, n-butanol, isobutanol, n-pentanol, n-hexanol, and the like. Most preferably, due to cost and the lower molecular weight of the resulting ester, the alcohol used for the esterification of the naphthalenedicarboxylic acid is methanol. The amount of methanol or other low-molecular weight alcohol that is reacted with the naphthalenedicarboxylic acid is an amount sufficient to convert a major portion of the naphthalenedicarboxylic acid to the diester. For example, the weight ratio of alcohol to naphthalenedicarboxylic acid added to the reactor is suitably about 1:1 to about 10:1; more preferably, 2:1 to about 6:1. A large molar excess of alcohol relative to the free carboxylic acid groups can provide for a more complete conversion of the naphthalenedicarboxylic acid to diester; however, the larger amount of alcohol requires the use of a large reaction mixture volume, which requires a larger reactor or slower throughput. Additionally, the excess methanol must be separated and recycled. It is, therefore, more advantageous to use lower weight ratios of alcohol to naphthalenedicarboxylic acid, such as about 1:1 to about 10:1, more preferably, 2:1 to about 6:1.

The alcohol, naphthalenedicarboxylic acid, and the PEN containing material are added to the esterification reactor to a reaction zone or reaction zones upstream from the reaction zone where the product mixture comprising the diester of the naphthalenedicarboxylic acid is removed from the series arranged reaction zones. The alcohol, the naphthalenedicarboxylic acid, and the PEN containing material are preferably added as a mixture. However, the naphthalenedicarboxylic acid, the low-molecular weight alcohol, or the PEN containing material can be added separately. Alternatively, only part of the alcohol can be added with the naphthalenedicarboxylic acid and the remainder of the alcohol added separately. Thus, in the process of this invention, any suitable method for adding the alcohol and naphthalenedicarboxylic acid and PEN containing material feed components to the esterification mixture is contemplated. However, it is most preferable to add the naphthalenedicarboxylic acid and PEN containing material to the reaction mixture as slurry with the alcohol, which slurry can be pumped into or otherwise added to the reaction mixture. By using the alcohol to slurry the solid naphthalenedicarboxylic acid and PEN containing material, it is possible to add the naphthalenedicarboxylic acid and PEN containing material to the reaction mixture without using recycled diester to slurry the naphthalenedicarboxylic acid. This is one of the advantages of the present invention. In the prior art processes where the alcohol and the naphthalenedicarboxylic acid are added counter-currently, rather than co-currently, the naphthalenedicarboxylic acid had to be slurried with a relatively large amount of diester. Consequently, a large part of the crude diester product would need to be recycled to the front end of the process to provide the slurry medium for the fresh naphthalenedicarboxylic acid. Such recycling is an inefficient operation. In contrast, in the instant invention with the cocurrent addition of the alcohol and the naphthalenedicarboxylic acid and PEN containing material, there is enough conversion to the diester of the naphthalenedicarboxylic acid in the initial upstream reaction zone to provide a liquid medium for the esterification reaction. The weight ratio of alcohol to naphthalenedicarboxylic acid in the slurry is suitably about 1:1 to about 10:1, preferably about 1.5:1 to about 6:1.

The mixture of alcohol and naphthalenedicarboxylic acid and PEN containing material is first pre-heated before the mixture is added to the series arranged esterification reaction zones. A stirred tank reactor, a tubular heat exchanger, or a combination thereof can function as a preheater. The preheater heats the mixture of alcohol and naphthalenedicarboxylic acid and PEN containing material to a temperature typically below the esterification temperature. For example, temperatures in the range of about 300° F. to about 700° F. are suitable. When methanol is used, the temperature of the preheater is preferably below the critical temperature of methanol. All of the alcohol charged to the esterification reaction mixture can be added through the preheater. Alternatively, only part of the total alcohol charged to the mixture is added through the preheater, and the remainder is added to the esterification reaction mixture either directly or through a separate preheater.

The naphthalenedicarboxylic acid and PEN containing material can also be added to the esterification reaction mixture or, if used, the preheater, along with a monoalkyl ester of a naphthalenedicarboxylic acid, a dialkylester of a naphthalenedicarboxylic acid, or a combination of mono- and dialkylester of naphthalenedicarboxylic acid. If used, the weight ratio of the mono- or dialkyl naphthalenedicarboxylic acid ester (or mixture thereof) to naphthalenedicarboxylic acid is suitably about 0.01:1 to about 1:1, and more preferably about 0.1:1 to about 0.5:1. The naphthalenedicarboxylic acid and PEN containing material can be pre-mixed with the mono- and/or dialkylester of naphthalenedicarboxylic acid before it is added to the reactor or preheater. Alternatively, the naphthalenedicarboxylic acid and PEN containing material can be added to the reactor or preheater separately from the addition of the mono- and/or dialkyl ester of naphthalenedicarboxylic acid.

Esterification reaction temperatures in the range of about 500° F to about 700° F., preferably about 540° F. to about 660° F., provide for rapid reaction rates without significant decomposition of the starting naphthalenedicarboxylic acid or dialkylester product. At these high reaction temperatures, the esterification reaction is rapid and long reaction residence times are not required. Each reaction zone may be operated at the same, or at different temperatures.

The pressure used for the esterification reaction is suitably in the range of about 5 to about 250, and preferably about 20 to about 150 atmospheres absolute. When practicing the process of this invention, it is preferable to use reaction conditions such as temperature and pressure, so that the reactor is not completely liquid-filled, i.e., where there is at least some alcohol present is in the gaseous phase in the reactor rather than having all of the alcohol be present in the liquid phase. When practicing this preferred mode, one reaction zone, rather a series of zones, can be used. It is preferable, however, to use at least two reaction zones in series. Thus, in the preferred series arranged zones, one or more reaction zone preferably contains a gaseous alcohol stream moving through the reaction zone, preferably through the liquid component of the reaction mixture, the liquid component being mainly the product dialkylester of naphthalenedicarboxylic acid along with varying amounts of the mono ester of the naphthalenedicarboxylic acid, and the PEN containing material. When operating within conditions where a portion of the alcohol is in the gaseous phase, we have determined that a much smaller total reactor volume can be used to complete the esterification reaction. Under conditions where part of the alcohol is in the gas phase, the gaseous alcohol can move through the series arranged reaction zones very rapidly, and the reactor volume can be used more efficiently. The result being that a much smaller reactor volume can be used. Additionally, the gaseous alcohol, preferably methanol, moving through the single reaction zone or preferably the series arranged reaction zones, removes a portion of the water formed during the esterification reaction and allows for a greater conversion of the diacid to the desired dialkylester.

Furthermore, we have determined that when the esterification reaction is conducted such that a major portion of the alcohol added to the reaction mixture is in the gaseous state, there is only a very low formation of dialkylether. Apparently, most of the dialkylether formation occurs in a liquid phase reaction, possibly catalyzed by the acidic esterification reaction mixture. By suitably adjusting reaction conditions, such as reaction temperature and reaction pressure, it is highly advantageous to operate such that about 50 to about 99%, preferably about 80 to about 98%, of the alcohol charged to the reaction mixture is in the vapor or gaseous state rather than being liquid in the esterification reactor. Thus, by suitably adjusting reaction conditions and after correcting for alcohol consumed in the esterification reaction, the ratio of the rate of gaseous alcohol, preferably methanol, passing through the esterification reaction zones from the upstream to the downstream reaction zone, and preferably through the liquid phase of the esterification reaction mixture, in pounds per hour, to the rate of addition of alcohol to the reaction mixture in pounds per hour, is about 0.5:1 to about 0.99:1, preferably about 0.8:1 to about 0.98:1. Stated differently, preferably about 50 to about 99%, more preferably about 80 to about 98% of the total alcohol exiting a reactor zone in the esterification reactor, is in the gaseous state. Suitable pressures for such operation are in the range of about 5 atmospheres absolute to about 250 atmospheres absolute, along with temperatures in the range of about 500° F. to about 700° F.

The esterification reaction according to the process of this invention can be conducted with or without one or more standard esterification catalysts. However, it is preferable not to use an esterification catalyst. One of the advantages of the process of this invention is the ability to conduct the esterification reaction without the addition of an esterification catalyst. Thus, it is preferable to conduct the esterification reaction in the substantial and, more preferably, complete absence of an esterification catalyst. Should one or more standard esterification catalysts be included, it is preferable to use molybdenum trioxide, zinc, zinc oxide, a titanate ester, or an organo tin compound.

The residence time for the liquid portion of the esterification reaction mixture in the process of this invention is suitably about 0.1 hours to about 10 hours, and preferably about 0.1 hours to about 2 hours.

In the process of this invention, two reaction zones in series can be used to perform the esterification reaction. Preferably, about 2 to about 20, most preferably about 3 to about 15, reaction zones are used in series. The reaction zones are equipped such that the esterification reaction mixture can flow between zones from the initial reaction zone to the terminal reaction zone. At least one of the reaction zones is agitated to provide for the suspension of the solids present in the reaction zone. Preferably, all of the reaction zones are agitated with a suitable stirrer or other means for agitating a liquid phase. A pump circulating the liquid phase within the reaction zone can also serve to agitate the contents of a reaction zone. The reaction zones are suitably tank reactors, preferably stirred tank reactors, plug flow reactors, or a combination of these or other reactors. As discussed in more detail below, a particularly preferred configuration for the series arranged reaction zones is a vertically arranged compartmented reactor having two or more compartments segregated by a divider plate or other separating means that allows for the passage of the esterification reaction mixture from a lower compartment to an upper compartment. As described below, one such compartmented reactor having a plurality of compartments can be used. Alternatively, two or more of such compartmented reactors can be used in series to achieve series arranged reaction zones according to the process of this invention. Regardless of the specific apparatus used for a reaction zone, the reactors must be able to withstand the temperatures and pressures used in the process of this invention. Also, the construction of the reactors should be such that it will withstand the effects of exposure to the corrosive esterification reaction mixture. Consequently, the parts of the reactor vessels exposed to the esterification reaction mixture can be manufactured of materials such as 316 stainless steel or a nickel-based alloy, such as Hastelloy C. The reaction zones can have equal or different volumes. Preferably, the first reaction zone is larger than the subsequent zones so that it provides for a longer residence time and greater conversion of the naphthalenedicarboxylic acid and PEN containing material to diester.

The preferred reactor configuration is a vertically arranged, cylindrical vessel that is divided into at least an upper and a lower compartment, each compartment functioning as a reaction zone. Preferably, the vessel is divided into about 2 to about 20, most preferably about 3 to about 15 compartments. Each compartment is separated from the adjacent compartment by a plate or other suitable means for dividing the reactor vessel into compartments. Each plate or other divider means is provided with at least one opening to allow for the passage of liquid, solid and, if present, gaseous components of the esterification reaction mixture from one compartment to the next, while the esterification reaction mixture passes in an upward direction through the reactor vessel. The low molecular weight alcohol and the naphthalenedicarboxylic acid and PEN containing material are added to a lower compartment and a reaction product mixture containing the diester of the naphthalenedicarboxylic acid is removed from an upper reactor compartment. The area of the opening relative to the area of the divider plate is such that the esterification reaction mixture can pass through the opening without causing an excessive backpressure, and yet prevent substantial back-flow of the esterification reaction mixture to the previous compartment. A suitable opening in the divider plate comprises about 0.1 to about 10% of the area of the dividing plate or other dividing means. Preferably, an agitator shaft runs vertically through the reactor vessel, preferably along the center line of the reactor vessel (if it is a cylindrical vessel) and at least one agitator is attached to the agitator shaft in at least one and, preferably, all of the compartments. An agitator located in each compartment provides for mixing and the suspension of insoluble matter in the esterification reaction mixture that would otherwise lead to the formation of deposits that could decrease the reactor volume, severely restrict the flow of the esterification reaction mixture and eventually plug the reactor. The reactor vessel can also be equipped with baffles positioned within one or more of the compartments. One configuration is to have the baffles positioned so that they are normal to the inside surface of the reactor and run the entire length of the reactor. Other configurations of the baffles are also suitable, for example, the baffles can extend only part way from the bottom of each compartment.

The PEN containing materials react with the low molecular weight alcohol, preferably methanol, which is present in excess to form crude DM-2,6-NDC which can be recovered and purified. The crude DM-2,6-NDC derived from the PEN containing materials may be processed along with the main flow of crude DM-2,6-NDC that was made from reaction of methanol with NDA. The ethylene glycol by-product and products derived from the reaction of ethylene glycol with itself or with the low molecular weight alcohol may be processed out of the unit as a consequence of normal solvent processing and purging of impurities using any suitable techniques. The DM-2,6-NDC purification step generally comprises one or more purification procedures such as recrystallization, distillation, and combinations thereof. Other impurities which are present in the PEN, for example, corrosion metals or polymerization catalyst residues such as antimony, are economically removed by the same unit operations which purify the DM-2,6-NDC produced by the main normal process flow to its final form.

The valuable naphthalate component of PEN, which can contain various contaminants, can be recovered by adding the PEN-containing materials to the feed to the esterification reactor. The PEN reacts with excess methanol present in the reactor to afford crude DM-2,6-NDC and ethylene glycol by means of cleavage and transesterification reactions. Because of the conditions in and design of the esterification reactor, no new catalyst or other components are needed to accomplish the cleavage and transesterification reactions. This is a benefit because if no new ingredients are added for reaction, they need not be subsequently removed.

The degree of PEN conversion in the reactor is likely to be extremely high. It is likely, however, that the conversion of PEN containing materials to DM-2,6-NDC will be less than 100%. Thus there is a need to have the ability to remove partial reaction products, for example various glycol esters or contaminants which could cause color or lead to ash or particulate contamination, from the final purified DM-2,6-NDC. In addition, the ethylene glycol by-product and other contaminants such as antimony or other inorganic residues in the PEN containing material may not be allowed to contaminate DM-2,6-NDC. The numerous steps of purification which follow the reactor step, and the steps which provide solvent recovery and recycle provide these functions economically. Since the purification capabilities of the esterification section are so robust, no new purification equipment needs to be added.

The esterification reaction product mixture typically comprises a mixture of DM-2,6-NDC and, depending on the weight ratio of methanol to 2,6-NDA, various levels of monomethyl-2,6-naphthalenedicarboxylate (MM-2,6-NDC). The esterification reaction product mixture also contains some residual PEN or related by-products, ethylene glycol, methanol, water, organic impurities, and solubilized oxidation catalyst metals. Because the DM-2,6-NDC is more soluble in methanol than 2,6-NDA, the DM-2,6-NDC is in solution in the hot esterification reaction mixture. The MM-2,6-NDC is also typically in solution.

After the esterification reaction is completed, the esterification reaction mixture is cooled to crystallize the DM-2,6-NDC contained therein. The cooling can be accomplished by any suitable means. However, the cooling is most efficiently accomplished by a pressure reduction with the consequent evaporation of methanol cooling the esterification reaction mixture. This can be accomplished in one zone, or it can be accomplished in a series of cooling zones. In a batch mode operation, the esterification reaction vessel can be used to crystallize the DM-2,6-NDC. Although the temperature to which the esterification reaction mixture is cooled is variable and depends, in part, upon the ratio of methanol to 2,6-NDA used in the esterification reaction and the desired degree to which the DM-2,6-NDC is to be crystallized from the methanol, the esterification reaction mixture is typically cooled to a temperature not greater than about 50° C., preferably to a temperature in the range of about 10° C. to about 40° C., and most preferably to a temperature of about 20° C. to about 30° C. Cooling the reaction mixture to these temperatures can be suitably accomplished by subjecting the esterification reaction mixture to a vacuum, thus accelerating evaporative cooling and achieving temperatures below the normal boiling point of methanol. All or part of the evaporated methanol may be condensed by cooling, and then returned to the crystallization vessel. Other suitable methods for cooling the mixture can be used, however, such as using cooling coils cooled by chilled water. Cooling the reaction mixture to these temperatures assures that a major portion of the DM-2,6-NDC crystallizes from solution. Preferably at least about 75 percent and more preferably at least about 90 percent of the DM-2,6-NDC in the esterification reaction mixture crystallizes from solution.

After the DM-2,6-NDC crystallizes, it is partitioned from the esterification reaction mother liquor. This can be accomplished by any suitable means for partitioning solids from liquids such as filtration, centrifugation or settling. Unreacted 2,6-naphthalenedicarboxylic acid and MM-2,6-NDC also typically precipitate during the cooling and are collected with the DM-2,6-NDC.

Along with the esterification reaction mother liquor, most of the impurities, such as brominated products, esterified FNA, solubilized catalyst metals, water produced in the esterification reaction, ethylene glycol, and yet unidentified oxidation and esterification/transesterification reaction intermediates and reaction side products are rejected. The esterification reaction mother liquor is, however, mainly unreacted methanol used for the esterification reaction. This methanol can be recovered from the mother liquor and used for recycle to one or more of the other process steps.

If the oxidation catalyst metals are permitted to remain in the DM-2,6-NDC purification process stream, they concentrate in the distillation bottoms. If the DM-2,6-NDC is injected into the distillation column at a point within the distillation column packing, the oxidation catalyst metals will rapidly and possibly irreversibly plug the distillation column. Also, when oxidation catalyst metals are allowed to concentrate in the distillation bottoms, they can produce a highly viscous material that is not easily removed by, for example, a purge stream. Periodic cleaning would therefore necessitate the discontinuance of the distillation process. Therefore, these catalyst metals must be removed in order to provide for the efficient distillation of DM-2,6-NDC. Furthermore, it is desirable to recycle to the esterification reactor at least part and preferably substantially all of the distillation bottoms to recover any DM-2,6-NDC and/or MM-2,6-NDC contained therein. If the catalyst metals are not removed, they will only increase in concentration in the distillation bottoms with recycle and aggravate the aforementioned problems.

Crystallized DM-2,6-NDC collected by filtration, centrifugation, or that obtained from some other means used for partitioning the crystallized product from the esterification reaction mother liquor, is preferably washed with methanol, mixtures of methanol and water, or other suitable solvent such as a $C_5$-$C_{10}$ hydrocarbon, i.e., pentanes, hexanes, toluene, xylenes, cyclohexane, etc. A $C_6$-$C_{10}$ halogenated aromatic such as chlorobenzene, or a $C_1$-$C_4$ carboxylic acid such as acetic and propionic acid, and mixtures of these acids with water are also suitable solvents for washing the crystallized esters. This washing step removes additional impurities and results in purer DM-2,6-NDC, particularly if the solvent used to wash the DM-2,6-NDC is at an elevated temperature. Most preferably, the solvent used to wash the crystallized DM-2,6-NDC is methanol, or a mixture of methanol and water. The weight ratio of solvent, preferably methanol or methanol/water mixture, to the DM-2,6-NDC used for washing is in the range of about 0.2:1 to about 2:1, respectively.

The crystallized DM-2,6-NDC is preferably subjected to a recrystallization procedure for further purification. Recrystallization is accomplished by contacting the DM-2,6-NDC with methanol or other suitable recrystallization solvent and maintaining the resulting recrystallization mixture at an elevated temperature to dissolve at least a portion of the DM-2,6-NDC and preferably at least about 75 percent and more preferably at least about 90 percent of the DM-2,6-

NDC. A pressure vessel can be used to heat the mixture to a temperature above the normal boiling point of the solvent. A suitable weight ratio of recrystallization solvent to DM-2,6-NDC is in the range of about 1:1 to about 10:1, and preferably about 2:1 to about 6:1, respectively.

Methanol is the preferred recrystallization solvent because it is used in the esterification reaction and it can be treated and recycled along with other methanol process streams. These amounts of methanol are generally sufficient to dissolve the DM-2,6-NDC at reasonable temperatures and provide a recrystallized product suitable for the next stage of purification. However, as mentioned above, other recrystallization solvents are suitable. For example, $C_6$-$C_{10}$ aromatic solvents such as benzene, toluene, o-, m- or p-xylene, a mixture of xylenes, ethylbenzene, cumene, pseudocumene, and the like, are also suitable as recrystallization solvents. Halogenated $C_6$-$C_{10}$ aromatic compounds such as chlorobenzene are also suitable. The xylenes are particularly preferred aromatic recrystallization solvents. The preferred temperature for dissolving the DM-2,6-NDC in the recrystallization solvent is in the range of about 80° C. to about 190° C.

After the DM-2,6-NDC and the recrystallization solvent are maintained at an elevated temperature so that at least a portion of the DM-2,6-NDC is dissolved, the resulting mixture is cooled to a recrystallization temperature to recrystallize the dissolved DM-2,6-NDC. Cooling is accomplished by any suitable means such as using cooling coils within the vessel used for the recrystallization. However, it is preferable from the standpoint of cost in a plant operation to reduce the pressure and allow the mixture to cool by evaporative cooling. If the dissolution of the DM-2,6-NDC in the recrystallization solvent is accomplished at temperatures above the normal boiling point of the recrystallization solvent, the pressure need only be reduced to lower the temperature of the mixture to the desired recrystallization temperature. However, attaining temperatures below the normal boiling point of the solvent by evaporative cooling requires the application of a vacuum to the vessel or apparatus holding the recrystallization solution. The recrystallization temperature is any temperature that allows for the recrystallization of at least a portion of the DM-2,6-NDC. Preferably, the recrystallization temperature is not greater than about 50° C., more preferably in the range of about 10° C. to about 40° C. and most preferably about 20° C. to about 30° C.

Upon recrystallization of the solid DM-2,6-NDC, it is partitioned from the recrystallization solvent (mother liquor) by any suitable means for partitioning solids from liquids such as, for example, settling, centrifugation, vacuum or pressure filtration, etc. If methanol is used as a solvent, the filtrate can be recycled to the esterification reactor. Alternatively, it can be treated to remove the methanol and the remaining heavy high boiling components can be recycled to the esterification reactor or discarded. If a solvent other than methanol is used as the recrystallization solvent, it too can be treated to remove heavies and then purified for reuse. Solid recrystallized DM-2,6-NDC collected on the filter, centrifuge, etc. is preferably washed, preferably with the solvent used for the recrystallization step, or other suitable solvent such as those discussed hereinabove used to wash the crystallized DM-2,6-NDC. Washing removes additional impurities particularly if the washing solvent is at an elevated temperature. The weight ratio of solvent to DM-2,6-NDC used to wash the recrystallized DM-2,6-NDC is suitably in the range of about 0.2:1 to about 2:1, respectively. Depending on variables such as the amount of time the DM-2,6-NDC remains in the centrifuge, vacuum filter, pressure filter or other partitioning device, the pressure (or vacuum) applied, and the solvent used for recrystallization and/or washing, etc., the DM-2,6-NDC filter cake will contain variable amounts of solvent. This solvent can, if desired, be removed by one or more drying techniques such as heating in a sweep of air or inert gas, use of a vacuum with or without additional heating, or other suitable means for drying the DM-2,6-NDC. It is preferred, however, to heat the DM-2,6-NDC, optionally at reduced pressure, until it becomes molten and simultaneously distilling any excess solvent from the DM-2,6-NDC. Molten DM-2,6-NDC, preferably free of substantially all of the solvent used for the recrystallization and/or washing, is distilled in the next step of the process.

Although only one recrystallization step has been described, it will be apparent to a person skilled in the art that one or more additional recrystallization procedures, depending on the degree of purity required, can be used. These additional procedures may occur with or without a washing step, and may use the same or different recrystallization and washing solvents. Additionally, while the DM-2,6-NDC is in solution in the recrystallization solvent, it can be treated with one or more physical or chemical means for stabilizing the DM-2,6-NDC or for removing impurities. For example, it can be treated with an oxidizing agent such as air, a peroxide, hydroperoxide or peracid. It can be treated with a reducing agent. It can also be treated with a base such as an alkoxide, e.g., sodium methoxide, or calcium, sodium or potassium hydroxide, carbonate or bicarbonate. Sodium methoxide provides for superior color DM-2,6-NDC when added in an amount of about 0.1 to about 2 weight percent based on the weight of DM-2,6-NDC in the recrystallization solvent.

Molten crystallized or recrystallized ester is distilled in at least one distillation step. Due to the high melting point of DM-2,6-NDC (approximately 190° C.), the temperature of the distillation is necessarily above about 190° C. Also, because DM-2,6-NDC deteriorates in purity, and particularly in color, by being maintained at excessive temperatures, it is preferable to conduct the distillation at reduced pressure. Distillation tower bottoms are therefore suitably in the range of about 190° C. to about 310° C., and preferably about 210° C. to about 290° C. Distillation pressure can range from about 2.5 torr to about 200 torr. Preferably, the distillation pressure is in the range of about 6 to about 100 torr.

The distillation can be a simple distillation. However, to attain the highest purity of DM-2,6-NDC, it is preferable to use a fractionating column. The fractionating column can be packed with random or structured column packing designed to increase the liquid-vapor contact in the column. Fractionation columns having trays, e.g. sieve trays or bubble cap trays, which are well known in the distillation art, are also suitable.

Distillation of the DM-2,6-NDC removes undesirable heavy high boiling impurities, such as residual MM-2,6-NDC, various colored by-products, residual catalyst metals, and other possible residues from the PEN containing material. Importantly, the distillation removes particulate contaminants from the DM-2,6-NDC. Particulate contaminants are difficult to remove from the DM-2,6-NDC unless a distillation step is employed. For example, even if the DM-2,6-NDC is dissolved in a suitable solvent, filtered and recrystallized, the solid DM-2,6-NDC must be collected by filtration or centrifugation and is also usually dried to free the DM-2,6-NDC of excess recrystallization solvent. These operations introduce particulate contaminants to the DM-2,6-NDC. Consequently, the distillation procedure of this invention as the final purification procedure assures that the DM-2,6-NDC contains low levels of particulate contaminants, levels that are suitable for manufacturing PEN that can be used for fabricating high quality thin films. Preferably, the distillation step provides for DM-2,6-NDC containing less than about 5000 and more preferably less than about 2000 particles greater than about 1.5 microns in size per gram of DM-2,6-NDC as measured by a HIAC/ROYCO particle analyzer instrument. The distilled molten DM-2,6-NDC is optionally cooled and solidified in a suitable apparatus such as a flaker.

It is to be understood that the hereinabove described process for preparing purified DM-2,6-NDC can be conducted such that each process step is operated in either a batch or continuous manner. For a large-scale, commercial operation, it is preferable to conduct the entire process in a continuous manner, where the process described herein is conducted in series arranged reaction and process zones.

EXAMPLE #1

Batch experiments were conducted by adding PEN containing materials for recycle at specific selected conditions to a batch reactor which was simultaneously accomplishing the high-temperature uncatalyzed esterification reaction of crude 2,6-naphthalenedicarboxylic acid (NDA) to crude dimethyl 2,6-naphthalenedicarboxylate (DM-2,6-NDC). These results are described below.

a) Effect of residence time at fixed concentration of PEN film scrap, 5 wt % PEN based on crude NDA feed. These runs show a high conversion of PEN at all residence times, as evidenced by the low concentration of glycol esters measured in the isolated crude reaction product. The conversion of crude NDA to crude DM-2,6-NDC is also high, as evidenced by the lack of detectable carboxylic acids in the isolated crude reaction product.

| Run # | Batch residence time, minutes | Crude product composition, wt % glycol esters | Crude product composition, wt % methyl esters | Crude product composition, wt % carboxylic acids |
|---|---|---|---|---|
| 1 | 20 | 0.19 | 99.81 | 0 |
| 2 | 10 | 0.26 | 99.74 | 0 |
| 3 | 5 | 0.56 | 99.44 | 0 | b) Effect of PEN concentration, all other variables held constant. These runs show a high conversion of PEN film scrap at all concentrations and residence times, as evidenced by the low concentrations of glycol esters measured in the isolated crude reaction product. The conversion of crude NDA to crude DM-2,6-NDC is also high, as evidenced by the lack of detectable carboxylic acids in the isolated crude reaction product.

| Run # | Wt % PEN scrap based on crude NDA | Crude product composition, wt % glycol esters | Crude product composition, wt % methyl esters | Crude product composition, wt % carboxylic acids |
|---|---|---|---|---|
| 20 minutes batch residence time ||||
| 4 | 5 | 0.19 | 99.81 | 0 |
| 5 | 2 | 0.06 | 99.94 | 0 |
| 6 | 1 | 0.04 | 99.96 | 0 |
| 10 minutes batch residence time ||||
| 7 | 10 | 0.47 | 99.54 | 0 |
| 8 | 5 | 0.26 | 99.74 | 0 |
| 9 | 1 | 0.03 | 99.97 | 0 | c) Effect of PEN homopolymer scrap physical form, all other variables held constant, is shown by means of the following analyses of the isolated crude reaction product. These runs show comparable results, irrespective of particle size of the PEN homopolymer scrap.

| Run # | PEN particle size | Crude product composition, wt % glycol esters | Crude product composition, wt % methyl esters | Crude product composition, wt % carboxylic acids |
|---|---|---|---|---|
| 10 | Native chip | 0.22 | 99.78 | 0 |
| 11 | 500µ diameter | 0.24 | 99.77 | 0 |
| 12 | 250µ diameter | 0.16 | 99.83 | 0 |

EXAMPLE #2

PEN homopolymer scrap containing approximately 250 ppmw antimony and other trace contaminants was introduced at approximately 5 wt % of the crude 2,6-naphthalenedicarboxylic acid feed to a commercial continuous reactor producing dimethyl 2,6-naphthalenedicarboxylate via a high-temperature high-pressure uncatalyzed esterification reaction with methanol. The unit was operating steps of reaction and the subsequent steps of product recovery, product purification, and solvent recovery in the normal manner in all respects.

After allowing the continuous unit to attain a lined-out condition, samples of the crude reactor effluent slurry were analyzed for evidence of unreacted PEN. The results showed approximately 90% conversion of PEN had occurred in the reactor along with the normal esterification reaction of 2,6-NDA to DM-2,6-NDC. Samples of the final purified product DM-2,6-NDC were analyzed for evidence of unreacted PEN, for antimony residues, for ethylene glycol, and for typical DM-2,6-NDC quality attributes. Typical DM-2,6-NDC quality attributes are as follows. The sum of organic impurities is calculated by combining the measured concentrations of MM-NDC, NDA, and the methyl ester of FNA. Acid number is a calculated value which is indicative of the quantity of unesterified carboxylic acid residues remaining in the DM-2,6-NDC product. Ash, an indicator of inorganic (metal) residues in the product, is measured by reducing the sample to a carbonaceous residue by burning and then ashing in a muffle furnace. Color, reported on the American Public Health Association (APHA) scale, is indicative of the whiteness of the DM-2,6-NDC product. The foreign particle test is a measure of the degree of product contamination by particulate material by particles having diameter greater than 1.5 microns.

These results demonstrated that the test product met all normal quality specifications and was indistinguishable from the product made in the absence of added PEN homopolymer scrap. No special techniques were required to manage product quality to meet normal specifications. The ethylene glycol residues from PEN methanolysis were purged from the unit and were non-detectable in the DM-2, 6-NDC product. Glycol esters, which would be evidence of contamination of product with traces of unreacted PEN, were not detected in the final purified DM-2,6-NDC product. Other residual materials contained in the PEN, for example the antimony residues from PEN manufacture, were non-detectable in the final purified DM-2,6-NDC product. This example demonstrates that the superior reaction and purification capabilities of the process accomplished the cleavage and transesterification reaction of PEN scrap, accomplished the normal reaction of 2,6-NDA to DM-2,6-NDC, and maintained DM-2,6-NDC quality, but incurred no added processing costs.

| DM-2,6-NDC Quality Attribute | Product made with PEN homopolymer recycle | Product made without PEN homopolymer recycle |
| --- | --- | --- |
| Sum of organic impurities | 203 ppmw | 205 ppmw |
| Acid number | 0.001 mg KOH/g | 0.001 mg KOH/g |
| Ash | 0.8 ppmw | 0.7 ppmw |
| Color | 35 APHA units | 39 APHA units |
| Foreign particles | 510 particles/gram | 477 particles/gram |

The process shall be described for the purposes of illustration only in connection with certain embodiments. However, it is recognized that various changes, additions, improvements, and modifications to the illustrated embodiments may be made by those persons skilled in the art, all falling within the scope and spirit of the invention.

That which is claimed is:

1. A process for preparing a dialkylester of a naphthalenedicarboxylic acid comprising directing a liquid phase reaction mixture comprising a low molecular weight alcohol, a naphthalenedicarboxylic acid, a dialkylester of a naphthalenedicarboxylic acid, and a material having polyethylene naphthalate at a temperature range of about 500° F. to about 700° F. and at a pressure in the range of about 5 to about 250 atmospheres absolute through reaction zones arranged in succession while introducing a naphthalenedicarboxylic acid, a material having polyethylene naphthalate and a low molecular weight alcohol to an upstream reaction zone, agitating at least one reaction zone, and removing a product having a dialkylester formed by the reaction of the naphthalenedicarboxylic acid and the material having polyethylene naphthalate with the low molecular weight alcohol from a downstream reaction zone.

2. The process of claim 1 wherein the material having polyethylene naphthalate comprises up to about 20 weight percent of said naphthalenedicarboxylic acid.

3. The process of claim 1 wherein there are about 2 to about 20 reaction zones.

4. The process of claim 1 wherein the low molecular weight alcohol is methanol, the naphthalenedicarboxylic acid is 2,6-naphthalenedicarboxylic acid and the dialkylester produced is dimethyl-2,6-naphthalenedicarboxylate.

5. The process of claim 1 wherein most of the alcohol added to the reaction zones arranged in succession is present in the reaction zones in a gas phase.

6. The process of claim 1 wherein each reaction zone is equipped with an agitator to agitate the liquid phase reaction mixture present in the reaction zone.

7. The process of claim 1 wherein the reaction zones are stirred tank reactors.

8. The process of claim 1 wherein the process is performed in a batch or continuous manner.

9. A process for preparing a dialkylester of a naphthalenedicarboxylic acid comprising contacting a low molecular weight alcohol, a naphthalenedicarboxylic acid, and a material having polyethylene naphthalate in a liquid esterification reaction mixture comprising a dialkylester of the naphthalenedicarboxylic acid, at a temperature in the range of about 500° F. to about 700° F. and at a pressure in the range of about 5 to about 250 atmospheres absolute in a vertically arranged, compartmented reactor having at least an upper and lower compartment, the compartments being separated by a dividing means having an opening to permit the upward flow of the esterification reaction mixture between reactor compartments, and where the low molecular weight alcohol and the naphthalenedicarboxylic acid and the material having polyethylene naphthalate are added to a lower compartment or compartments, and a reaction product mixture having a diester of naphthalenedicarboxylic acid is removed from an upper reactor compartment.

10. The process of claim 9 wherein the compartmented reactor comprises about 2 to about 20 compartments.

11. The process of claim 10 wherein all of the compartments are equipped with an agitator to agitate the liquid reaction mixture present in the compartment.

12. The process of claim 9 wherein the low molecular weight alcohol is methanol, the naphthalenedicarboxylic acid is 2,6-naphthalenedicarboxylic acid and the product mixture comprises dimethyl-2,6-naphthalenedicarboxylate.

13. The process of claim 9 wherein at least a portion of the alcohol added to the compartmented reactor passes through the compartmented reactor as gaseous alcohol.

14. The process of claim 13 wherein most of the alcohol added to the compartmented reactor is in the liquid phase and in the form of a slurry with the naphthalenedicarboxylic acid.

15. The process of claim 10 wherein the compartmented reactor comprises about 3 to about 8 compartments.

16. The process of claim 12 wherein most of the methanol added to the compartmented reactor passes through the reactor in a gaseous state.

17. The process of claim 9 wherein the esterification reaction temperature is in the range of about 540° F. to about 660° F. and the pressure is about 20 atmospheres absolute to about 150 atmospheres absolute.

18. The process of claim 12 wherein the weight ratio of methanol to 2,6-naphthalenedicarboxylic acid added to the compartmented reactor is in the range of about 1:1 to about 10:1.

19. The process of claim 18 wherein most of the methanol, most of the 2,6-naphthalenedicarboxylic acid, and most of the material having PEN added to the compartmented reactor is in the form of a slurry of the 2,6-naphthalenedicarboxylic acid in liquid methanol.

20. The process of claim 9 wherein the material having polyethylene naphthalate comprises up to about 20 weight percent of the naphthalenedicarboxylic acid.

21. A process for preparing a dialkylester of a naphthalenedicarboxylic acid comprising contacting the naphthalenedicarboxylic acid, and a material having polyethylene naphthalate, with a low molecular weight alcohol in a suitable reaction zone and in a reaction mixture comprising a liquid dialkylester of a naphthalenedicarboxylic acid, a naphthalenedicarboxylic acid, a material having polyethylenenaphthalate and a low molecular weight alcohol, under reaction conditions where the low molecular weight alcohol is present in the reaction mixture in both the liquid and the gas phase, where low molecular weight alcohol is added to the reaction zone and simultaneously removed from the reaction zone such that the ratio of the rate of removal of the alcohol in pounds per hour from the reaction zone in the gas phase to the rate of addition of the alcohol to the reaction zone in pounds per hour is about 0.5:1 to about 0.99:1.

22. The process of claim 21 wherein the alcohol is methanol, the naphthalenedicarboxylic acid is 2,6-naphthalenedicarboxylic acid and the liquid dialkylester of a naphthalenedicarboxylic acid is dimethyl-2,6-naphthalenedicarboxylate.

23. The process of claim 21 wherein the material having polyethylene naphthalate comprises up to about 20 weight percent of the naphthalenedicarboxylic acid.

24. A process for preparing a purified dialkylester of a naphthalenedicarboxylic acid comprising:
   (a) crystallizing the dialkylester by cooling a reaction mixture comprising a low molecular weight alcohol, a naphthalenedicarboxylic acid, a dialklester of a naphthalenedicarboxylic acid, and a material having polyethylene naphthalate and partitioning crystallized dialkylester from the reaction mixture mother liquor containing solubilized residual oxidation catalyst
   (b) dissolving the crystallized dialkylester in a recrystallization solvent at a temperature in the range of about 80° C. to about 190° C., to form a recrystallization mixture,
   (c) recrystallizing dialkylester by cooling the recrystallization mixture and partitioning recrystallized dialkylester from recrystallization mother liquor,
   (d) vacuum distilling the recrystallized dialkylester such that the distilled dialkylester contains less than about 5000 particles greater than about 1.5 microns in size per gram of distilled dialkylester; and
   (e) recovering the distilled dialkylester.

25. The process of claim 24 wherein the low molecular weight alcohol is methanol, the naphthalenedicarboxylic acid is 2,6-naphthalenedicarboxylic acid and the product mixture comprises dimethyl-2,6-naphthalenedicarboxylate.

26. The process of claim 24 wherein the reaction mixture of step (a) is cooled to a temperature not greater than about 50° C. to crystallize the dimethyl-2,6-naphthalenedicarboxylate.

27. The process of claim 24 wherein the recrystallization mixture of step
   (c) is cooled to a temperature not greater than about 50° C.

28. The process of claim 24 wherein the recrystallization solvent is methanol, a $C_6$-$C_{10}$ aromatic or a halogenated $C_6$-$C_{10}$ aromatic.

29. The process of claim 24 wherein after step (a) the crystallized dimethyl-2,6-naphthalenedicarboxylate is washed with a solvent.

30. The process of claim 24 wherein after step (c) the partitioned recrystallized dimethyl-2,6-naphthalenedicarboxylate is washed with a solvent.

31. The process of claim 24 wherein the vacuum distillation is conducted using a fractionation column.

32. The process of claim 31 wherein the fractionation column is packed with a structured packing.

33. The process of claim 24 wherein the process is performed in a batch or continuous manner.

34. The process of claim 24 wherein impurities are rejected along with the mother liquors of steps (a) and (c).

35. The process of claim 28 wherein the recrystallization solvent is recycled to the reaction mixture prior to step (a).

* * * * *